United States Patent [19]

Umeda et al.

[11] Patent Number: 5,779,941
[45] Date of Patent: Jul. 14, 1998

[54] 1,2-N-ACYL-N-METHYLENE-ETHYLENEDIAMINE, AND ELECTROCONDUCTIVE PASTE COMPRISING IT

[75] Inventors: Hiroaki Umeda; Tsunehiko Terada; Hisatoshi Murakami, all of Osaka, Japan

[73] Assignee: Tatsuta Electric Wire and Cable Co., Ltd., Osaka, Japan

[21] Appl. No.: 844,817

[22] Filed: Apr. 22, 1997

[30] Foreign Application Priority Data

Apr. 26, 1996 [JP] Japan ................................ 8-106957
Apr. 26, 1996 [JP] Japan ................................ 8-106958
Oct. 29, 1996 [JP] Japan ................................ 8-286292

[51] Int. Cl.$^6$ .......................... H01B 1/22; C07C 233/00
[52] U.S. Cl. .......................... 252/512; 564/182; 564/192
[58] Field of Search .......................... 252/512, 514; 564/182, 192

[56] References Cited

U.S. PATENT DOCUMENTS

| | | |
|---|---|---|
| 4,326,067 | 4/1982 | Fazio ................................ 548/347 |
| 4,855,497 | 8/1989 | Takagi et al. .................... 564/182 |
| 5,136,365 | 8/1992 | Pennisi et al. ................... 357/72 |

FOREIGN PATENT DOCUMENTS

| | | |
|---|---|---|
| 239901 | 10/1987 | European Pat. Off. . |
| 455019 | 11/1991 | European Pat. Off. . |
| 1311019 | 3/1973 | United Kingdom . |

OTHER PUBLICATIONS

Patent Abstracts of Japan vol. 018, No. 282 (C-1205), May 30, 1994 & JP 06 049272 A (Nippon Oil & Fats Co Ltd), Feb. 22, 1994, abstract.

*Primary Examiner*—Mark Kopec
*Attorney, Agent, or Firm*—Jordan and Hamburg

[57] ABSTRACT

Novel compounds, 1,2-N-acyl-N-methylene-ethylenediamines of formula (I) are useful as dispersants, rust inhibitors, curing promoters for epoxy resins, electroconductivity-imparting agents, mold lubricants, etc.

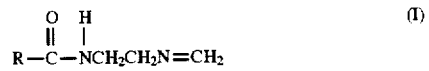

$$R-C(=O)-N(CH_2CH_2N=CH_2)H \quad (I)$$

where R is a hydrogen atom or a hydrocarbon group.

An electroconductive paste with excellent electroconductivity and much improved long-term stability is obtained by mixing 100 parts by weight of a thermosetting resin with from 250 to 900 parts by weight of a metal filler and from 1 to 50 parts by weight of the 1,2-N-acyl-N-methylene-ethylenediamine; or by adding from 250 to 900 parts by weight of a metal filler coated with the 1,2-N-acyl-N-methylene-ethylenediamine to 100 parts by weight of a thermosetting resin.

6 Claims, 5 Drawing Sheets

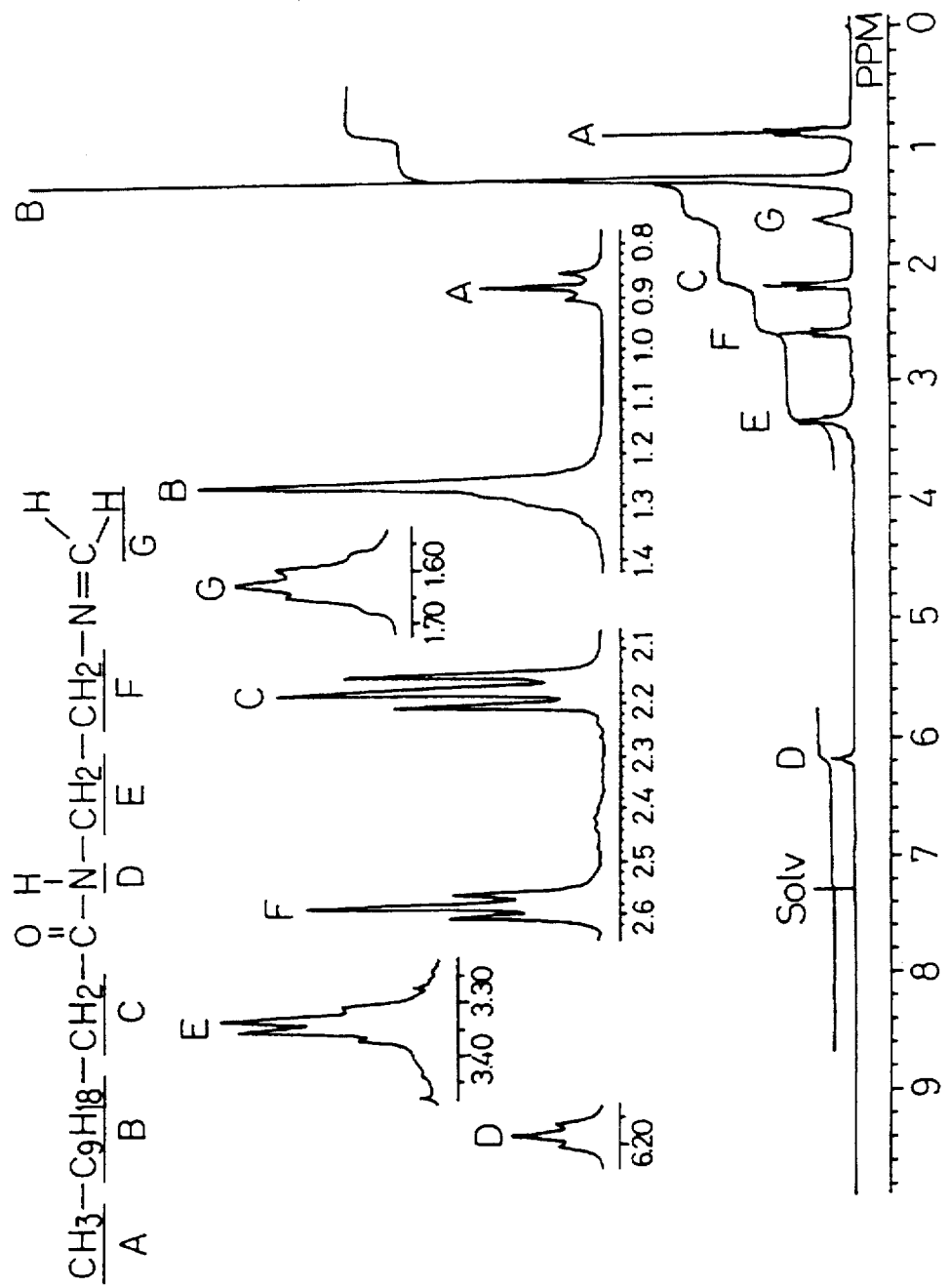

1,2-N-ACYL-N-METHYLENE-ETHYLENEDIAMINE, AND ELECTROCONDUCTIVE PASTE COMPRISING IT

TECHNICAL FIELD

The present invention relates to novel compounds, 1,2-N-acyl-N-methylene-ethylenediamines. It also relates to an electroconductive paste that is used in producing printed circuit boards for preventing the boards from making noise while in actual use and for mounting constitutive parts on the boards, and the paste comprises said compound and has improved electroconductivity and long-lasting reliability.

BACKGROUND ART

As the filler to be in electroconductive pastes that are used in producing printed circuit boards for preventing the boards from making noise while in actual use and for mounting constitutive parts on the boards, oxidation-resistant silver, silver-coated copper powder, nickel and the like have heretofore been being much used. The pastes comprising silver or silver-coated copper powder have high electroconductivity and oxidation resistance. However, they are expensive and their migration is often problematic. On the other hand, the pastes comprising nickel have low electroconductivity, though having good oxidation resistance, and therefore their use is limited. As opposed to these, pastes comprising copper powder as the filler are inexpensive and there is no problem about their migration. However, these are problematic in that the copper powder existing in them is oxidized whereby the electroconductivity of the pastes is lowered with the lapse of time.

On the other hand, in order to obtain electroconductive pastes having good adhesiveness to printed circuit boards, epoxy resins have heretofore been being used as the binder in the pastes. However, the use of epoxy resins is problematic in that the pastes could not have satisfactory electroconductivity.

The present invention provides novel compounds, 1,2-N-acyl-N-methylene-ethylenediamines and provides an electroconductive paste comprising the compound. The electroconductive paste of the invention, as comprising the compound, 1,2-N-acyl-N-methylene-ethylenediamine, is free from the above-mentioned problems. Specifically, even when a filler with poor oxidation resistance, such as copper powder, is used in the paste, the paste can still maintain good electroconductivity and high reliability for a long period of time. In particular, the electroconductive paste of the invention has good electroconductivity and good adhesiveness.

DISCLOSURE OF THE INVENTION 1,2-N-acyl-N-methylene-ethylenediamines of the present invention are represented by the following general formula (I):

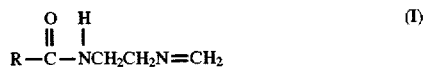

wherein R represents a hydrogen atom or a hydrocarbon group.

The hydrocarbon group may includes, aliphatic hydrocarbon groups and aromatic hydrocarbon groups. As examples of the groups, mentioned are alkyl groups such as methyl, ethyl and propyl groups; cycloalkyl groups such as cyclopentyl and cyclohexyl groups; and aralkyl groups such as benzyl and phenethyl groups. However, these are not limitative.

As comprising the above-mentioned compound, 1,2-N-acyl-N-methylene-ethylenediamine, the electroconductive paste of the invention can have good electroconductivity and long-lasting reliability even when it contains a filler with poor oxidation resistance, such as copper powder.

Preferably, the electroconductive paste of the present invention comprises 100 parts by weight of a thermosetting resin, from 250 to 900 parts by weight of a metal filler and from 1 to 50 parts by weight of the above-mentioned compound, 1,2-N-acyl-N-methylene-ethylenediamine, or comprises 100 parts by weight of a thermosetting resin and from 250 to 900 parts by weight of a metal filler coated with the compound, 1,2-N-acyl-N-methylene-ethylenediamine. In the latter, the amount of the compound, 1,2-N-acyl-N-methylene-ethylenediamine to be used for coating the metal filler is preferably from 0.05 to 5% by weight of the metal filler.

The thermosetting resin is preferably an epoxy resin, or a mixture comprising an epoxy resin and one or more selected from alkyd resins, melamine resins, phenolic resins and xylenic resins, as realizing the object of the invention of providing electroconductive pastes having good adhesiveness and good electroconductivity.

BRIEF DESCRIPTION OF THE DRAWINGS

FIG. 5 is an FT-NMR spectral pattern of the above-mentioned product.

Figure 1:
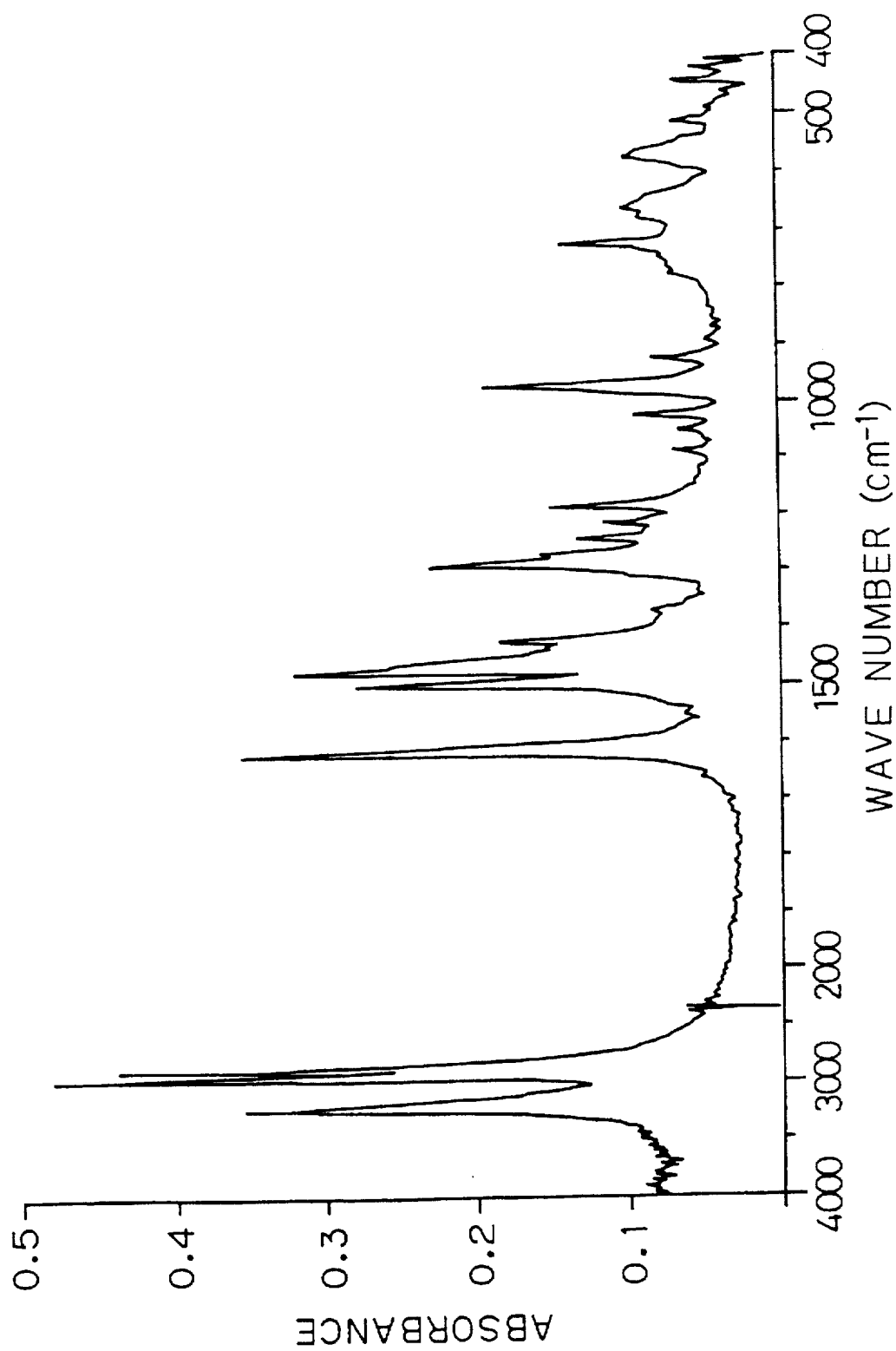
FIG. 1 is a Fourier transform infrared spectral pattern of 2-undecylimidazoline used in Production Example 1.

BEST MODES OF CARRYING OUT THE INVENTION 1,2-N-acyl-N-methylene-ethylenediamines of the above-mentioned general formula (I) may be obtained, for example, according to the following reaction process. Briefly, an imidazoline compound of formula (II) is hydrolyzed to give an N-acyl-1,2-diamine of formula (III); and the N-acyl-1,2-diamine is reacted with formaldehyde. In the following formulae, R has the same meaning as above, or that is, represents a hydrogen atom or a hydrocarbon group.

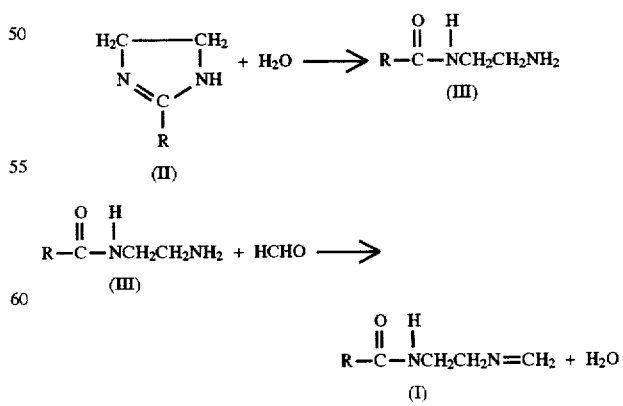

Some examples are referred to. 1,2-N-formyl-N-methylene-ethylenediamine of formula (I) where R is H is obtained, starting from imidazoline to give N-formyl-1,2-diamine. 1,2-N-propionyl-N-methylene-ethylenediamine of formula (I) where R is a propyl group is obtained, starting from 2-propylimidazoline to give N-propionyl-1,2-diamine. 1,2-N-lauroyl-N-methylene-ethylenediamine of formula (I) where R is an undecyl group is obtained, starting from 2-undecylimidazoline to give N-lauroyl-1,2-diamine.

The above-mentioned compounds of the present invention. 1,2-N-acyl-N-methylene-ethylenediamines are useful, for example, as dispersants, rust inhibitors, curing promoters for epoxy resins, electroconductivity-imparting agents, mold lubricants, etc.

Now, electroconductive pastes comprising the above-mentioned compound, 1,2-N-acyl-N-methylene-ethylenediamine are referred to hereinunder.

The electroconductive paste of the present invention comprises a thermosetting resin and an electroconductive metal filler and is characterized in that it contains the above-mentioned compound, 1,2-N-acyl-N-methylene-ethylenediamine. In this, the type of the compound, 1,2-N-acyl-N-methylene-ethylenediamine is not specifically defined. However, in view of the easiness in their production and of their low costs, preferred are compounds of formula (I) where R is a hydrogen atom or an alkyl group having from 1 to 17 carbon atoms or so.

The thermosetting resin to be used in the present invention as the binder is preferably an epoxy resin, or a mixture comprising an epoxy resin and one or more selected from alkyd resins, melamine resins, phenolic resins and xylenic resins. As has been mentioned hereinabove, conventional electroconductive pastes comprising epoxy resins are problematic in that they could not have satisfactory electroconductivity, though having good adhesiveness. As opposed to these, the electroconductive pastes of the present invention have good adhesiveness and good electroconductivity.

Where a mixture comprising an epoxy resin and one or more selected from alkyd resins, melamine resins, phenolic resins and xylenic resins is used as the binder, the proportion of the additive resins to the epoxy resin is desirably not larger than 50% by weight of the mixture.

The type of the metal constituting the metal filler to be used in the present invention is not specifically defined. The size of the particles of the metal filler is not also specifically defined, but shall fall within the range of ordinary fillers. For example, the size may fall between 1 and 100 μm or so. The shape of the particles is not also specifically defined. For example, it may be any of spherical, flaky, dentric and amorphous ones. The metal fillers may be used either singly or in combination of two or more. Thus, the metal fillers for use in the present invention are not specifically defined. The most significant characteristic of the present invention is that even when a powdery filler, such as copper powder, having high electroconductivity but having poor oxidation resistance is used in the electroconductive paste of the invention, the paste can have good electroconductivity.

The electroconductive paste of the present invention shall indispensably comprise the above-mentioned components, a thermosetting resin, a metal filler and a 1,2-N-acyl-N-methylene-ethylenediamine, but may additionally contain any other additives, such as a dispersant, a viscosity-controlling agent, etc., provided that such additives do not interfere with the excellent characteristics of the paste.

As concrete means of incorporating an 1,2-N-acyl-N-methylene-ethylenediamine into an electroconductive paste comprising a thermosetting resin and a metal filler to prepare the electroconductive paste of the invention, referred to are two methods; one comprising directly adding the metal filler and the diamine compound to the resin followed by mixing them (hereinafter referred to as "addition method"), and the other comprising coating the metal filler with the diamine followed by adding the thus-coated filler to the resin (hereinafter referred to as "coating method").

In the former addition method, in general, from 250 to 900 parts by weight, preferably from 350 to 650 parts by weight of a metal filler and from 1 to 50 parts by weight of a 1,2-N-acyl-N-methylene-ethylenediamine may be added to and mixed with 100 parts of a thermosetting resin.

In this, if the amount of the metal filler to be added is less than 250 parts by weight, the resulting paste could not have the intended electroconductivity; but if it is more than 900 parts by weight, the amount of the resin to be in the paste shall be relatively small, often resulting in that the paste could not have the intended adhesiveness.

If the amount of the 1,2-N-acyl-N-methylene-ethylenediamine is less than 1 part by weight, the resulting paste could not have the intended electroconductivity; but if it is more than 50 parts by weight, such may have a negative influence on the moisture resistance of the paste.

As has been mentioned hereinabove, the electroconductive paste of the invention that comprises a predetermined amount of a 1,2-N-acyl-N-methylene-ethylenediamine has greatly improved electroconductivity and long-lasting reliability. Even if the paste comprises an easily-oxidizable filler such as copper powder, it can maintain its initial characteristics for a long period of time. Therefore, using the diamine compound, it is possible to obtain highly-reliable electroconductive pastes at low costs. If an epoxy resin or a mixture comprising an epoxy resin and one or more selected from alkyd resins, melamine resins, phenolic resins and xylenic resins is used as the thermosetting resin in the paste, the paste may have improved adhesiveness without sacrificing its electroconductivity.

Now, the latter coating method is referred to.

As the coating means for the method, mentioned are a wet process and a dry process.

The wet process comprises adding a powdery metal filler to a solution of a 1,2-N-acyl-N-methylene-ethylenediamine, stirring the resulting liquid, and thereafter removing the solvent through filtration or evaporation. The solvent to be used in this may be a polar solvent such as n-nonanoic acid, chloroform, m-cresol or the like. Of these, preferred is n-nonanoic acid.

The dry process comprises directly mixing and stirring a metal powder and a 1,2-N-acyl-N-methylene-ethylenediamine in a ball mill or the like. According to any of these processes, obtained is a metal filler coated with the diamine compound.

The amount of the diamine compound to be used for coating the metal filler may be generally from 0.05 to 5% by weight, preferably from 0.2 to 3% by weight, relative to the non-coated metal filler. If the amount is less than 0.05% by weight, such could not produce pastes having the intended long-lasting reliability. If, on the other hand, it is more than 5% by weight, such will often have a negative influence on the adhesiveness of the resulting pastes. The term "coating" as referred to herein indicates the condition of the powdery metal filler to be coated with a 1,2-N-acyl-N-methylene-ethylenediamine, in which the surfaces of the metal particles constituting the metal filler are almost completely coated with the diamine compound. It is ideal that the surfaces of the metal particles are entirely coated with the diamine compound. In practice, however, it is not always necessary that the entire surfaces of the particles are completely coated with the diamine compound, but the surfaces may be partly exposed if the thus partly-exposed filler particles are effective to realize the intended long-lasting reliability of the pastes comprising them.

The amounts of the thermosetting resin and the diamine-coated metal filler to be in the paste of the invention may be the same as those mentioned above, or that is, the paste may comprise 100 parts by weight of the thermosetting resin and from 250 to 900 parts by weight, preferably from 350 to 650 parts by weight, of the coated metal filler. In this, the weight of the coated-metal filler does not include the weight of the diamine compound.

The electroconductive paste as prepared according to the coating method exhibits the same effect as that prepared according to the addition method. However, in the coating method, since the metal filler is directly coated with a 1,2-N-acyl-N-methylene-ethylenediamine, the paste thus comprising the diamine-coated metal filler can have more excellent, long-lasting reliability and, in addition, is characterized in that it may contain a reduced amount of the diamine compound.

The addition method and the coating method can be combined herein, or that is, a part of the 1,2-N-acyl-N-methylene-ethylenediamine to be in the paste may be used for coating the metal filler while the remaining part of the diamine compound may be separately added to the paste comprising the diamine-coated metal filler. The paste thus prepared according to the combination of the two methods also produces the same good results as those mentioned above.

To prepare the electroconductive paste of the present invention, the above-mentioned constitutive components may be uniformly kneaded, for example, using a 3-roll mixer or the like. Through the kneading, the intended paste of the invention can be obtained with ease. The thus-obtained paste may be applied onto substrates, using a dispenser or according to screen printing, and cured thereon under heat.

The electroconductive paste of the present invention mentioned hereinabove is highly reliable and keeps its excellent electroconductivity for a long period of time. Therefore, the paste is favorably used in producing printed circuit boards for preventing the boards from making noise while in actual use, for mounting constitutive parts on the boards, and for filling via-holes in the boards.

In particular, when the surfaces of the filler particles are coated with a 1,2-N-acyl-N-methylene-ethylenediamine and the paste comprises the thus-coated filler, the long-lasting reliability of the paste is significantly improved. The paste having such greatly improved, long-lasting reliability can be used as a moisture-resistant electroconductive adhesive in various fields where moisture resistance is indispensable and where conventional, pure copper-containing electroconductive adhesives could not be used effectively.

Where an epoxy resin or a mixture comprising an epoxy resin and at least one selected from alkyd resins, melamine resins, phenolic resins and xylenic resins is used as the thermosetting resin, it is possible to obtain electroconductive pastes having excellent adhesiveness and excellent electroconductivity.

Now, the present invention will be described in more detail by means of the following examples, which, however, are not intended to restrict the scope of the invention.
(1) Production of 1,2-N-acyl-N-methylene-ethylenediamines Production Example 1:

50.0 g (0.223 mols) of 2-undecylimidazoline and 100 cc (5.57 mols) of distilled water were put into an egg-plant flask equipped with a Liebig condenser, and boiled therein for 1 hour. Using an evaporator, the resulting mixture was dried under a reduced pressure of 30 mmHg and at 80° C. for 1 hour to give a white solid.

This white solid was dissolved in 100 cc of methanol, to which was added, 19.3 g (0.223 mols) of formalin (aqueous solution of 37% formaldehyde). Then, the resulting mixture was left at room temperature for 30 minutes, whereby it gave a white precipitate.

The resulting white precipitate was taken out through filtration using filter paper (5C), washed twice with methanol, and then dried, using an evaporator, under a reduced pressure of 30 mmHg and at 80° C. for 1 hour to obtain a white solid. The final product had a melting point of 130° C., and its yield was 90%. Through its qualitative analyses mentioned below, this final product was identified to be the compound of formula (I) where R is undecyl group, or that is, 1,2-N-lauroyl-N-methylene-ethylenediamine.

Figure 2:
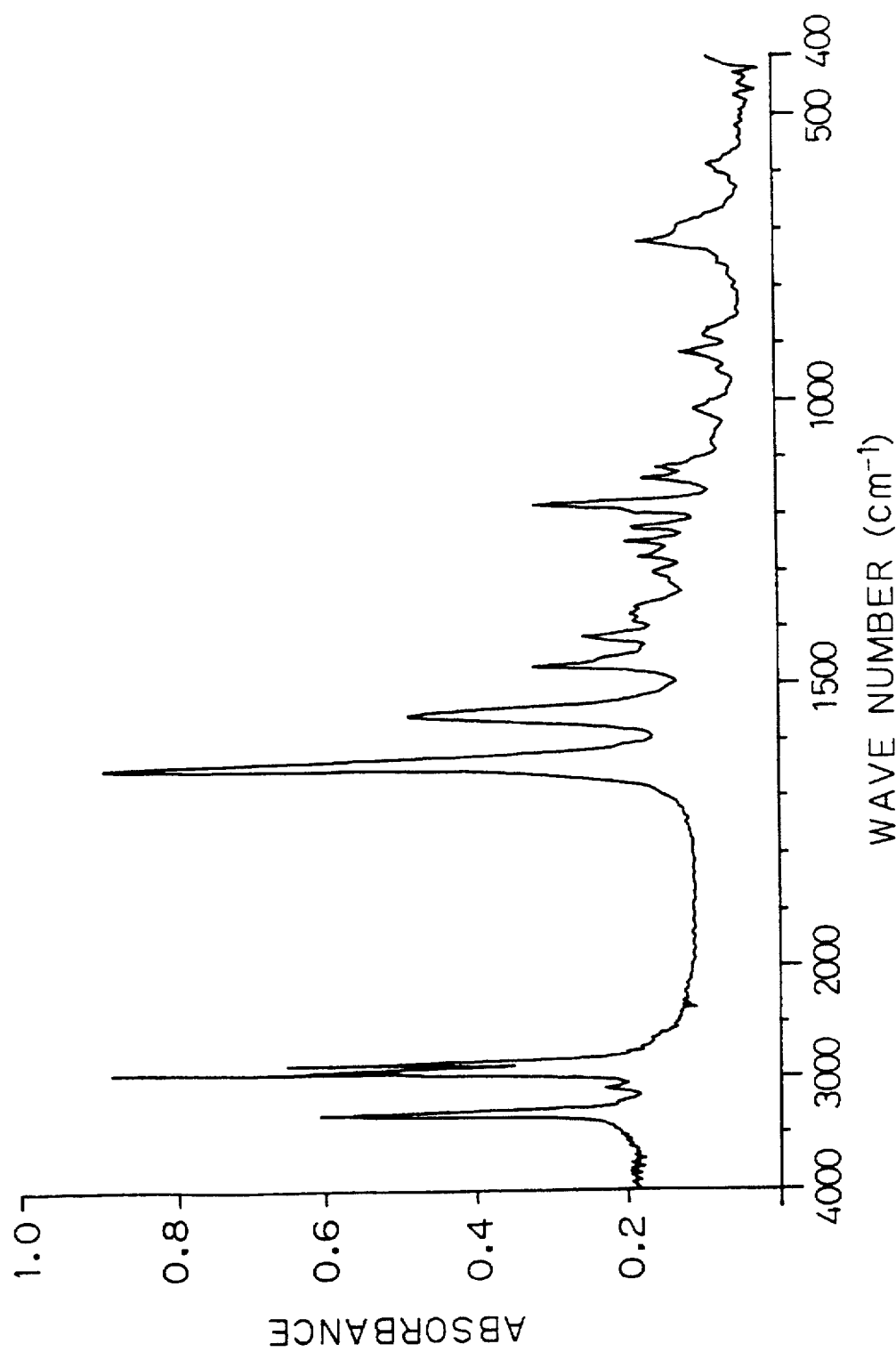
FIG. 2 is a Fourier transform infrared spectral pattern of the product in Production Example 1, 1,2-N-lauroyl-N-methylene-ethylenediamine.

① Fourier Transform Infrared Spectrometry:

Both the starting compound, 2-undecylimidazoline and the final product (hereinafter referred to as the product) in Production Example 1 were analyzed according to Fourier transform infrared spectrometry (using FT-IR-4100, produced by Shimadzu Corporation). The spectral patterns of the two are shown in FIG. 1 and FIG. 2. In the spectral pattern (FIG. 1) of 2-undecylimidazoline, seen is the absorption based on C=N and peculiar to the imidazoline ring within the range between 1400 and 1500 cm$^{-1}$; but in the spectral pattern (FIG. 2) of the product, said peak is not seen. In the latter, seen is the absorption based on C=O and peculiar to the amido bond at 1640 cm$^{-1}$.

Figure 3:
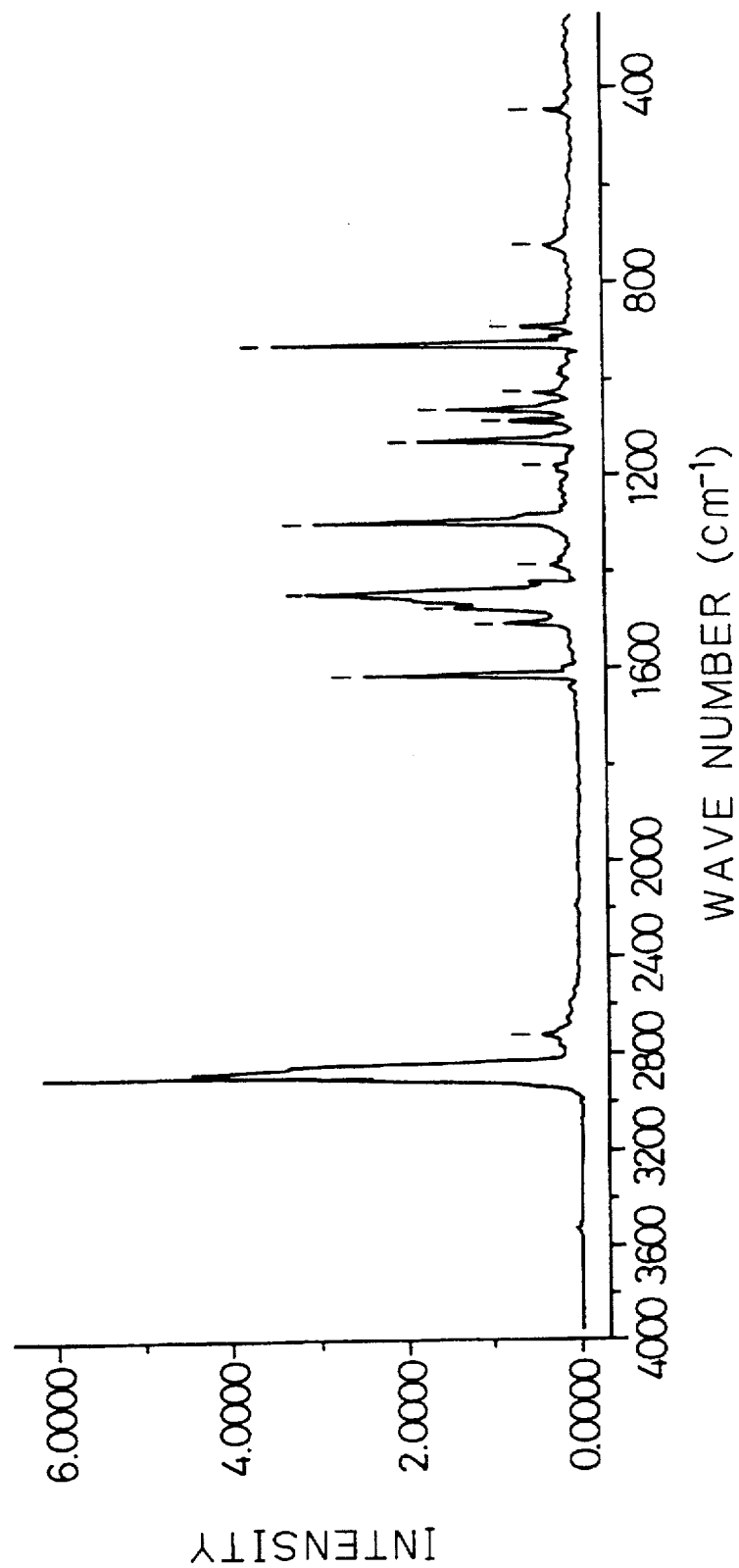
FIG. 3 is a Raman spectral pattern of 2-undecylimidazoline.
Figure 4:
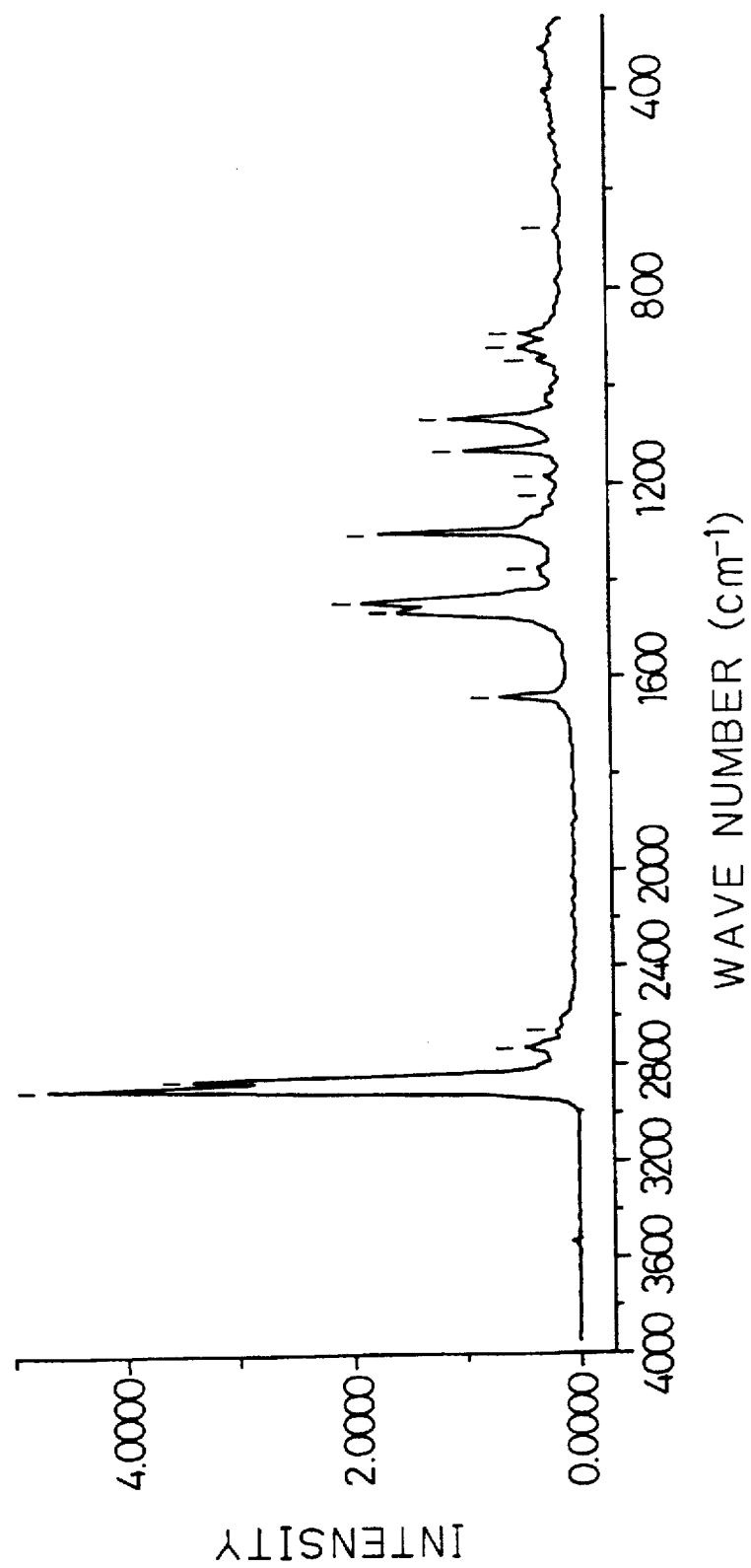
FIG. 4 is a Raman spectral pattern of the above-mentioned product.

② Raman Spectrometry;

2-Undecylimidazoline and the product were analyzed according to Raman spectrometry (using JRS-FT7000, produced by JEOL). The spectral patterns of the two are shown in FIG. 3 and FIG. 4. In the spectral pattern (FIG. 3) of 2-undecylimidazoline, seen is the peak based on the stretching vibration of the imidazoline ring at 923 cm$^{-1}$; but in the spectral pattern (FIG. 4) of the product, said peak is not seen.

③ FT-NMR Spectrometry:

The product was analyzed according to FT-NMR spectrometry (using FX200, produced by JEOL—in this was used a solvent, CDCl$_3$). The spectral pattern and the assignment for each signal are shown in FIG. 5.

④ Organic Elementary Analysis:

The product was analyzed, using an organic elementary analyzer (2400 Model, produced by Perkin Elmer). The analysis produced the data of 71% of C, 12% of H and 11% of N. These data correspond to the theoretical data as derived from the compositional formula ($C_{15}H_{30}N_2O$) of 1,2-N-lauroyl-N-methylene-ethylenediamine and its molecular weight of 254.

⑤ FAB (fast atom bombardment) mass spectrometry:

The product was analyzed according to PAB mass spectrometry (using JMS-HX100 in positive mode, produced by JEOL), which gave a peak for M/Z of 255. This peak was believed to be that for a pseudomolecular ion. From this, the molecular weight of the product was presumed to be 254, which corresponded to the molecular weight of 1,2-N-lauroyl-N-methylene-ethylenediamine.

Production Example 2:

In the same manner as in Production Example 1, except that 15.6 g (0.223 mols) of imidazoline was used as the starting compound in place of 2-undecylimidazoline, a white solid product was obtained herein. After having been subjected to the same qualitative analyses as in the above, this product was identified to be 1,2-N-formyl-N-methylene-ethylenediamine. The yield of the product was 90%.

Production Example 3:

In the same manner as in Production Example 1, except that 25.2 g (0.223 mols) of 2-propylirmidazoline was used as the starting compound in place of 2-undecylimidazoline, a white solid product was obtained herein. After having been subjected to the same qualitative analyses as in the above, this product was identified to be 1,2-N-propionyl-N-methylene-ethylenediamine. The yield of the product was 92%.

(2) Preparation of Electroconductive Pastes

Examples 1 to 9, Comparative Examples 1 and 2

Thermosetting resin, copper powder and 1,2-N-acyl-N-methylene-ethylenediamines were mixed in various ratios shown in Table 1 below to prepare various electroconductive pastes, which were tested to measure their specific resistance and tensile shear strength. The variation in the specific resistance of each paste sample was determined, which indicates the long-lasting reliability of the sample. The data obtained are shown in Table 1.

| Specific Resistance (ρ) (Ω·cm) = |Resistance (Ω)| × |(cross section of sample(s)) / (length of sample (1))| | (1) |
| Variation in Specific Resistance (%) = |(ρ' − ρ) / ρ| × 100 | (2) |

As is known from the data in Table 1, the samples containing a suitable amount of any of 1,2-N-acyl-N-methylene-ethylenediamines all had a specific resistance of $3 \times 10^{-4}$ or so, or that is, the electroconductivity of said samples is comparable to that of an ordinary electroconductive paste containing a silver filler. In addition, it is also known that the long-lasting reliability of these samples was much improved.

Examples 10 to 18, Comparative Examples 3 to 5:

Particles of copper powder were coated with 1,2-N-lauroyl-N-methylene-ethylenediamine according to any of the dry method and the wet method to be mentioned below. Varying amounts (shown in Table 2 below) of the thus-coated copper powder were added to various resin compo-

TABLE 1

| | Example | | | | | | | | | Comparative Example | |
|---|---|---|---|---|---|---|---|---|---|---|---|
| | 1 | 2 | 3 | 4 | 5 | 6 | 7 | 8 | 9 | 1 | 2 |
| Epoxy Resin (*1) | 100 | 80 | 80 | 80 | 90 | 100 | 100 | 100 | 100 | 100 | 100 |
| Alkyd Resin (*2) | — | 20 | — | — | — | — | — | — | — | — | — |
| Melamine Resin (*3) | — | — | 20 | — | — | — | — | — | — | — | — |
| Phenolic Resin (*4) | — | — | — | 20 | — | — | — | — | — | — | — |
| Xylenic Resin (*5) | — | — | — | — | 10 | — | — | — | — | — | — |
| Copper Powder | 370 | 370 | 370 | 370 | 370 | 370 | 370 | 300 | 850 | 370 | 370 |
| 1,2-N-hexanoyl-N-methylene-ethylenediamine | 45 | 7 | 7 | — | 7 | 45 | 1.5 | 7 | 7 | 0.5 | — |
| 1,2-N-propionyl-N-methylene-ethylenediamine | — | — | — | 7 | — | — | — | — | — | — | — |
| Specific Resistance (Ω·cm) | $3 \times 10^{-4}$ | $7 \times 10^{-4}$ | $8 \times 10^{-4}$ | $7 \times 10^{-4}$ | $5 \times 10^{-4}$ | $3 \times 10^{-4}$ | $7 \times 10^{-3}$ | $3 \times 10^{-3}$ | $5 \times 10^{-4}$ | $2 \times 10^{-1}$ | ∞ |
| Shear Strength (kgf/mm²) | 100 | 80 | 80 | 80 | 70 | 100 | 80 | 110 | 80 | 100 | 70 |
| Variation in Specific Resistance (%) | 150 | 200 | 250 | 200 | 200 | 150 | 200 | 150 | 150 | ∞ | — |

*1: EP-4940, ED-529, produced by Asahi Denka Kogyo KK
*2: EZ-3020-60-S; produced by Dai-Nippon Ink Chemical Industry Co.
*3: L-121-60, produced by Dai-Nippon Ink Chemical Industry Co.
*4: Resitop PL-2211 (MeOH), produced by Gun-ei Chemical Industry Co.
*5: Nikanol PR-1540, produced by Mitsubishi Gas Chemical Co.

The specific resistance shown in Table 1 above was measured as follows: Each electroconductive paste sample was printed on a glass/epoxy substrate according to a metal-printing method to form five circuit patterns thereon. The resistance between the both terminals of each pattern was measured, using a precision tester. From these data was obtained an average value. The specific resistance of each sample (p) was obtained according to the following equation (1).

The shear strength of each sample was obtained according to JIS K-6850, "Test Method for Tensile Shear Adhesion Strength of Adhesives".

The variation in specific resistance was obtained as follows: Each paste sample was exposed to an atmosphere of 95% RH at 60° C. for 500 hours in a thermostat, and the specific resistance (ρ') of the thus-exposed sample was measured. From the data, ρ (the original specific resistance of the non-exposed fresh sample) and ρ' (the specific resistance of the exposed sample), the variation in specific resistance of each sample was obtained according to the following equation (2).

sitions to prepare various electroconductive pastes, of which the characteristics were determined according to the same test methods mentioned above.

Dry Method for Examples 10, 12 to 18, and Comparative Examples 3 to 5:

Fine powder of 1,2-N-lauroyl-N-methylene-ethylenediamine, of which the amount is shown in Table 2, was added to 370 parts by weight of copper powder, and stirred in a defoaming machine for about 30 seconds.

Wet Method for Example 11:

0.8 g of 1,2-N-lauroyl-N-methylene-ethylenediamine was dissolved in 30 ml of n-nonanoic acid, then mixed with 370 g of copper powder by stirring then in a defoaming machine for 3 minutes, and finally dried under reduced pressure.

TABLE 2

|  | Example | | | | | | | | | Comparative Example | | |
|---|---|---|---|---|---|---|---|---|---|---|---|---|
|  | 10 | 11 | 12 | 13 | 14 | 15 | 16 | 17 | 18 | 3 | 4 | 5 |
| Epoxy Resin (*1) | 100 | 80 | 80 | 80 | 90 | 100 | 100 | 100 | 100 | 100 | 100 | 100 |
| Alkyd Resin (*2) | — | 20 | — | — | — | — | — | — | — | — | — | — |
| Melamine Resin (*3) | — | — | 20 | — | — | — | — | — | — | — | — | — |
| Phenolic Resin (*4) | — | — | — | 20 | — | — | — | — | — | — | — | — |
| Xylenic Resin (*5) | — | — | — | — | 10 | — | — | — | — | — | — | — |
| Copper Powder | 370 | 370 | 370 | 370 | 370 | 370 | 370 | 250 | 900 | 370 | 370 | 370 |
| 1,2-N-lauroyl-N-methylene-ethylenediamine (wt. %) | 5 | 0.8 | 0.8 | 0.8 | 0.8 | 0.05 | 0.8 | 0.8 | 0.8 | 0.04 | — | — |
| Oleic Acid (wt. %) | — | — | — | — | — | — | — | — | — | — | — | 0.8 |
| Specific Resistance ($\Omega \cdot cm$) | $3 \times 10^{-3}$ | $2 \times 10^{-3}$ | $8 \times 10^{-3}$ | $7 \times 10^{-3}$ | $5 \times 10^{-3}$ | $7 \times 10^{-3}$ | $8 \times 10^{-3}$ | $9 \times 10^{-3}$ | $2 \times 10^{-3}$ | $2 \times 10^{-2}$ | $<10^3$ | $2 \times 10^{-3}$ |
| Shear Strength (kgf/mm$^2$) | 120 | 110 | 115 | 110 | 117 | 117 | 110 | 115 | 100 | 110 | 110 | 110 |
| Variation in Specific Resistance (%) | −20 | −10 | −20 | −10 | −10 | 10 | −5 | −5 | −10 | 200 | ∞ | ∞ |

*1 to *5: Same as those in Table 1.

The specific resistance and the shear strength shown in Table 2 were obtained in the same manner as above. The variation in specific resistance was obtained as follows: Each paste sample was exposed to an atmosphere of 95% RH at 60° C. for 1000 hours in a thermostat, and the specific resistance (ρ') of the thus-exposed sample was measured. From the data, ρ (the original specific resistance of the non-exposed fresh sample) and ρ' (the specific resistance of the exposed sample), the variation in specific resistance of each sample was obtained according to the above-mentioned equation (2).

As is known from the data in Table 2, the variation in the specific resistance of the samples containing a suitable amount of 1,2-N-lauroyl-N-methylene-ethylenediamine, said samples having been subjected to the exposure test for 1000 hours, was not larger than 10%. Thus, the long-lasting reliability of these samples is comparable to that of an ordinary electroconductive paste containing a silver filler.

While the invention has been described in detail and with reference to specific embodiments thereof, it will be apparent to one skilled in the art that various changes and modifications can be made therein without departing from the spirit and scope thereof.

We claim:

1. 1,2-N-acyl-N-methylene-ethylenediamines of a general formula (I):

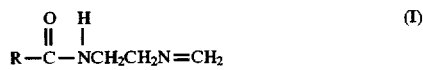

$$\begin{array}{c} O \quad H \\ \| \quad | \\ R-C-NCH_2CH_2N=CH_2 \end{array} \quad (I)$$

wherein R represents a hydrogen atom or a hydrocarbon group.

2. An electroconductive paste comprising a thermosetting resin, a metal filler and a 1,2-N-acyl-N-methylene-ethylenediamine of claim 1.

3. An electroconductive paste comprising 100 parts by weight of a thermosetting resin, from 250 to 900 parts by weight of a metal filler and from 1 to 50 parts by weight of a 1,2-N-acyl-N-methylene-ethylenediamine of claim 1.

4. An electroconductive paste comprising 100 parts by weight of a thermosetting resin and from 250 to 900 parts by weight of a metal filler coated with a 1,2-N-acyl-N-methylene-ethylenediamine of claim 1.

5. The electroconductive paste as claimed in claim 4, wherein the amount of the 1,2-N-acyl-N-methylene-ethylenediamine to be used for coating the metal filler therewith is from 0.05 to 5% by weight of the metal filler.

6. The electroconductive paste as claimed in any one of claims 2 to 5, wherein the thermosetting resin is an epoxy resin or a mixture comprising an epoxy resin and one or more selected from alkyd resins, melamine resins, phenolic resins and xylenic resins.

* * * * *